(12) United States Patent
Misle et al.

(10) Patent No.: US 10,028,768 B2
(45) Date of Patent: Jul. 24, 2018

(54) CANNULA AND NEEDLE ASSEMBLY

(71) Applicants: Gayle Misle, Millbrae, CA (US); Ryan C. Patterson, Farmington, UT (US); Trent J. Perry, Kaysville, UT (US)

(72) Inventors: Gayle Misle, Millbrae, CA (US); Ryan C. Patterson, Farmington, UT (US); Trent J. Perry, Kaysville, UT (US)

( * ) Notice: Subject to any disclaimer, the term of this patent is extended or adjusted under 35 U.S.C. 154(b) by 153 days.

(21) Appl. No.: 15/133,660

(22) Filed: Apr. 20, 2016

(65) Prior Publication Data
US 2017/0303956 A1 Oct. 26, 2017

(51) Int. Cl.
*A61M 5/178* (2006.01)
*A61B 17/34* (2006.01)
*A61M 25/06* (2006.01)
*A61B 17/00* (2006.01)

(52) U.S. Cl.
CPC ......... *A61B 17/3478* (2013.01); *A61M 25/06* (2013.01); *A61M 25/065* (2013.01); *A61M 25/0637* (2013.01); *A61B 2017/00792* (2013.01); *A61B 2017/347* (2013.01)

(58) Field of Classification Search
CPC ............ A61B 17/34; A61B 2017/347; A61M 25/00612; A61M 25/0637; A61M 25/0643; A61M 25/0606
See application file for complete search history.

(56) References Cited

U.S. PATENT DOCUMENTS

| 2,919,692 | A | | 1/1960 | Ackermann | |
|---|---|---|---|---|---|
| 5,676,656 | A | * | 10/1997 | Brimhall | ........... A61M 25/0606 604/162 |
| 2009/0054866 | A1 | | 2/2009 | Teisen-Simony et al. | |
| 2009/0259201 | A1 | * | 10/2009 | Hwang | ................. A61B 5/153 604/263 |

* cited by examiner

*Primary Examiner* — Rebecca E Eisenberg
(74) *Attorney, Agent, or Firm* — Dennis L. Thomte; Thomte Patent Law Office LLC (57) ABSTRACT

A cannula and needle assembly configured to first have the needle assembly create an opening in the skin of a person or animal and to then insert the cannula through the needle into the person or animal by way of the opening created by the needle. The assembly also includes structure to yieldably maintain the needle assembly in a docked position.

13 Claims, 8 Drawing Sheets

FIG. 11

CANNULA AND NEEDLE ASSEMBLY

BACKGROUND OF THE INVENTION

Field of the Invention

This invention relates to a cannula and needle assembly and more particularly to a means for the insertion of the cannula into various parts of a person such as knees, arms, shoulders, face, etc. The invention may also be used to insert a cannula into animals such as dogs, cats, etc.

Description of the Related Art

A cannula is usually defined as a flexible tube which is used to insert material or medicine into a vessel, duct or cavity of a person. The insertion end of the cannula is dull or blunt which makes it difficult to insert the cannula into the skin of the person. The usual method of inserting the cannula into the person is to first make an incision or hole in the person's skin with a needle. The needle is then removed from the incision or hole. The needle is then placed in its sleeve cap or is discarded. The injector then attempts to find the needle hole and then threads the cannula through the needle hole in the skin. Usually, the injector will use a larger needle than necessary to create a large hole in the person's skin so that the insertion of the cannula through the needle hole is somewhat easier.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

A cannula and needle assembly is disclosed wherein the cannula has a rearward end and a forward end. The cannula includes a mount having a rearward end and a forward end with a passageway, having rearward and forward ends, extending therebetween. The rearward end of the mount of the cannula is configured to be removably connected to a syringe. The forward end of the mount is tapered and has a plurality of regularly spaced-apart ribs protruding outwardly therefrom. The cannula also includes an elongated hollow shaft having a rearward end and a forward end with the rearward end of the hollow shaft being secured to the forward end of the mount whereby the rearward end of the hollow shaft is in communication with the forward end of the passageway in the mount.

The assembly also includes a needle portion having a needle hub having a rearward end and a forward end with the needle hub having a passageway formed therein which extends between the rearward and forward ends thereof. An elongated hollow needle, having a rearward end and a forward end, has its rearward end secured to the forward end of the needle hub whereby the needle is in communication with the forward end of the passageway extending through the needle hub. The forward end of the needle is sharpened. The needle hub also has a wing, having upper and lower ends, which extends therefrom. The rearward end of the needle hub has a plurality of radially spaced-apart slots formed therein and the needle hub is slidably mounted on the hollow shaft of the cannula whereby the shaft slidably extends through the rearward end of the needle hub, through the passageway in the needle hub and through the needle. The needle hub and needle are slidably movably mounted with respect to the hollow shaft and the mount between a first docked position and a second extended position. The slots in the rearward end of the needle hub receive the ribs of the mount therein to yieldably maintain the needle hub and the needle in the first docked position. The forward end of the needle is positioned rearwardly of the forward end of the shaft when the needle hub and the needle are in their first docked position. The forward end of the needle is positioned forwardly of the forward end of the cannula when the needle hub and the needle are in the extended position.

Other embodiments of the cannula and needle assembly are also described. The method of using the cannula and needle assembly of this invention to inject medicine or cosmetic materials into a person is described. The cannula and needle assembly of this invention may also be used to inject medicines or the like into an animal.

Therefore a principal object of the invention is to provide an improved cannula and needle assembly.

A further object of the invention is to provide a cannula and needle assembly wherein the needle assembly creates a hole in a person or an animal and which has the cannula slidably extending through the needle into the animal through the opening created by the needle with the needle being in place during the insertion of the cannula into the person or animal.

A further object of the invention is to describe a cannula and needle assembly which represents an advancement in the art.

A further object of the invention is to provide a cannula and needle assembly which is easy to use.

These and other objects will be apparent to those skilled in the art.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DESCRIPTION OF THE PREFERRED EMBODIMENT

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

A cannula and needle assembly is provided to enable an injector to insert a cannula into a patient or an animal. A first embodiment of the invention is shown in FIGS. 1-4. The method of using the first embodiment is illustrated in FIGS. 5-10. FIG. 11 illustrates a second embodiment of the invention.

Figure 5:
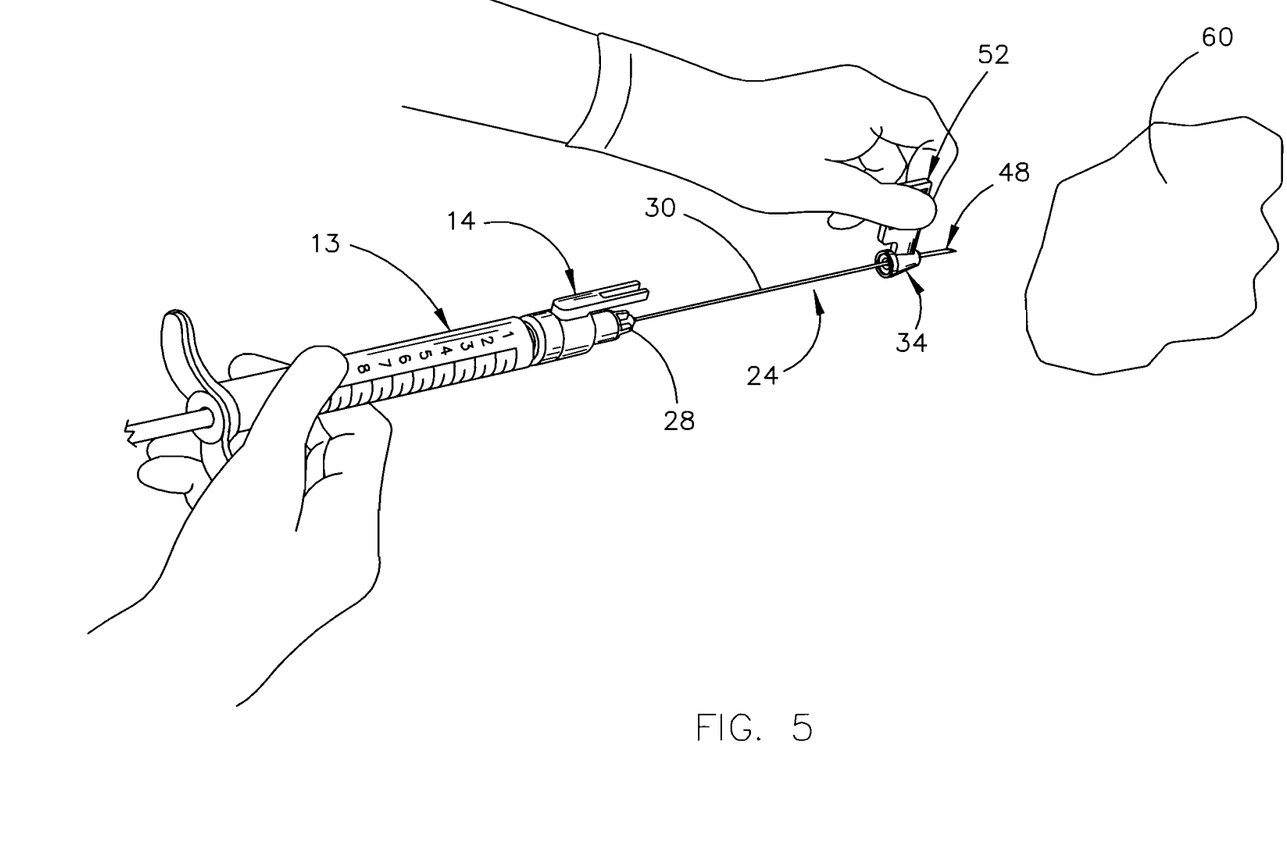
FIGS. 5-9 are perspective views which illustrate the method by which a cannula of this invention is inserted into a person or an animal.
Figure 6:
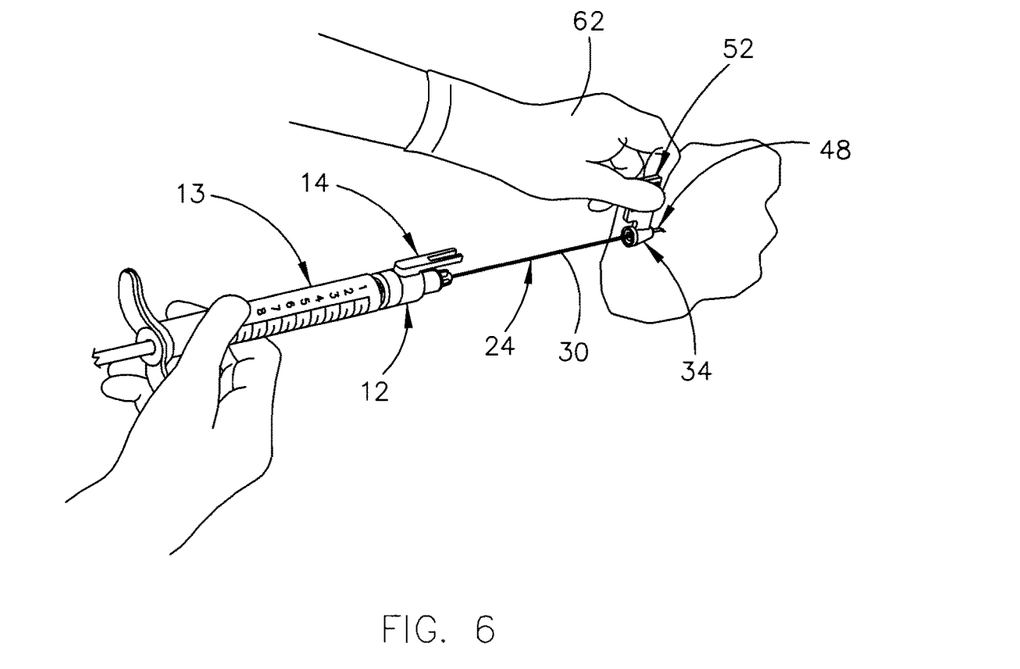
Figure 7:
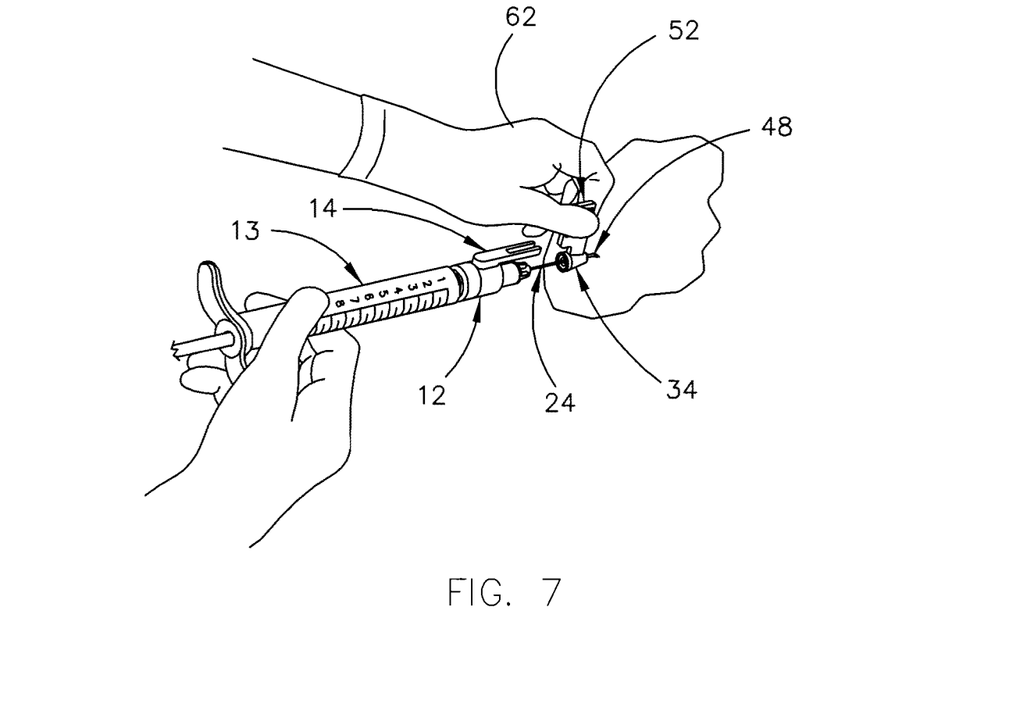

The numeral 10 refers to the cannula and needle assembly of FIGS. 1-4. Assembly 10 includes a universal syringe adapter 12 for connection to a syringe 13 (FIG. 5). Adapter 12 is of conventional design except for the needle dock 14 which is preferably molded with adapter 12. Needle dock 14 may be a separate part which is attached to syringe adapter 12 by any convenient means. Needle dock 14 includes a base 16 and a pair of forwardly extending and spaced-apart docking members or detents 18 and 20 which define an elongated slot or opening 22 therebetween.

The numeral 24 refers to the cannula of this invention. Cannula 24 includes a conventional mount 26 at its rearward end which is connected to syringe adapter 12 in conventional fashion. The forward end of mount 26 is tapered and has a plurality of notches or grooves 28 formed therein having ribs 29 therebetween. In this embodiment, the grooves 28 and ribs 29 are not required as will be explained hereinafter. Cannula 24 includes an elongated hollow shaft 30 which extends forwardly from mount 26 and usually has a blunt or dull forward end 32. Mount 26 and shaft 30 are hollow to permit medicines or cosmetic materials to pass therethrough.

The numeral 34 refers to the needle portion of the assembly 10. Needle portion 34 includes a forwardly tapered needle hub 36 having a bore 38 extending therethrough. Bore 38 includes an enlarged rearward bore portion 39 at its rearward end. A disc-shaped friction valve 40 is positioned in enlarged bore portion 39 of bore 38 and has a slit 42 formed therein. A friction valve retaining clip 44 is positioned in the enlarged bore portion 39 of bore 38 to retain friction valve 40 in place. Clip 44 has a central opening 46 formed therein through which shaft 30 of cannula 24 passes. Needle portion 34 also includes an elongated needle 48. The rearward end of needle 48 is secured to hub 36 and has a sharp point 50 at its outer end. Needle 48 is hollow and its rearward end is in communication with the forward end of bore 38. A wing 52 has one end thereof fixed to hub 36 and extends outwardly therefrom. Wing 52 includes a plurality of gripping members 54 formed therein. A recess 56 is formed in one side of wing 52 and a recess 58 is formed in the other side of wing 52.

The cannula and needle assembly 10 may be used to insert the cannula 24 into a patient or animal. The cannula 24 may be inserted into the knee, ankle, leg, arm, face, etc. of the patient. In FIG. 5, the skin 60 of a patient is illustrated. The manner in which the cannula 24 is inserted into the patient will now be described. First, the cannula 24 is removed from its protective sleeve or container and is secured to a syringe 13 in conventional fashion. The forward or outer end of shaft 30 of cannula 24 is then threaded or extended through bore 38 of needle hub 36 through friction valve 40 and through needle 48. The shaft 30 of cannula 24 frictionally engages the friction valve 40 in needle position 34 to prevent the needle portion from sliding up and down the cannula 24 when left unattended. Cannula 24 will be initially extended through needle 48 until the needle portion 34 is in the docked or retracted position of FIG. 1. In the docked position of FIG. 1, the wing 52 is received between the detents 18 and 20 with the outer or forward ends of detents 18 and 20 being received in the recesses 56 and 58 respectively to yieldably maintain the needle portion 34 in the docked position of FIG. 1.

Figure 1:
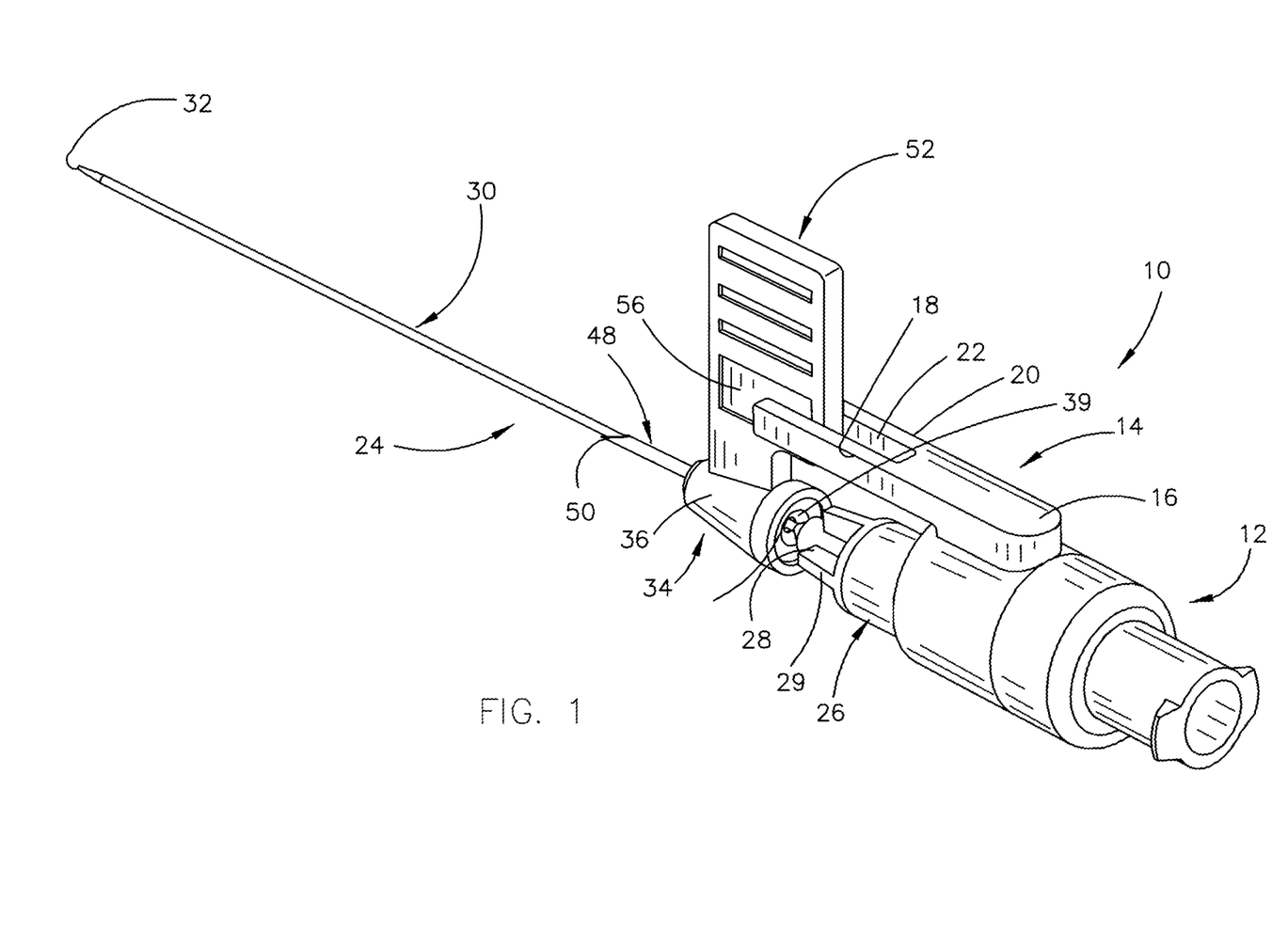
FIG. 1 is a perspective view of one embodiment of the invention with the needle portion of the invention being in its docked position.
Figure 2:
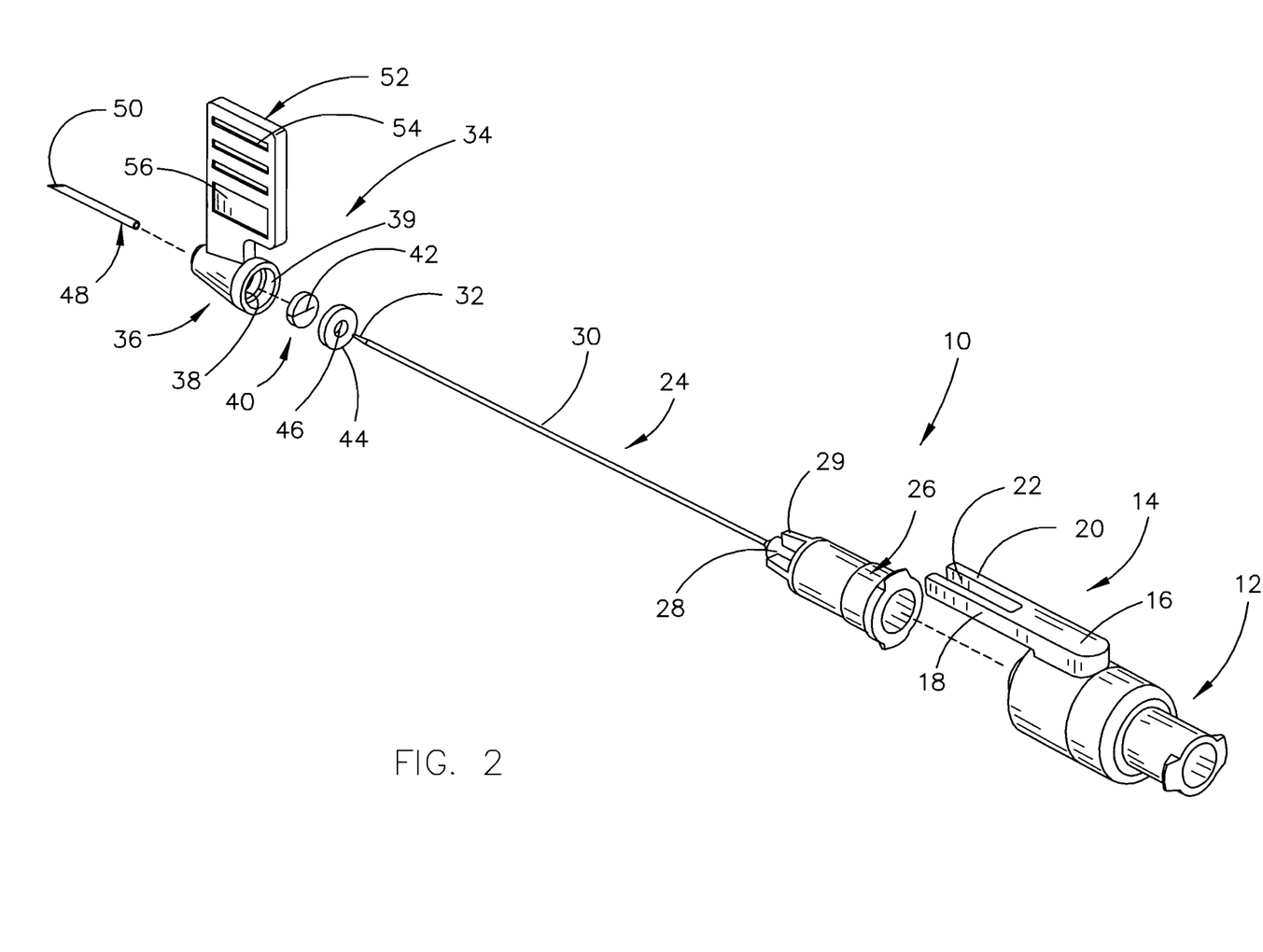
FIG. 2 is an exploded perspective view of the embodiment of FIG. 1.
Figure 3:
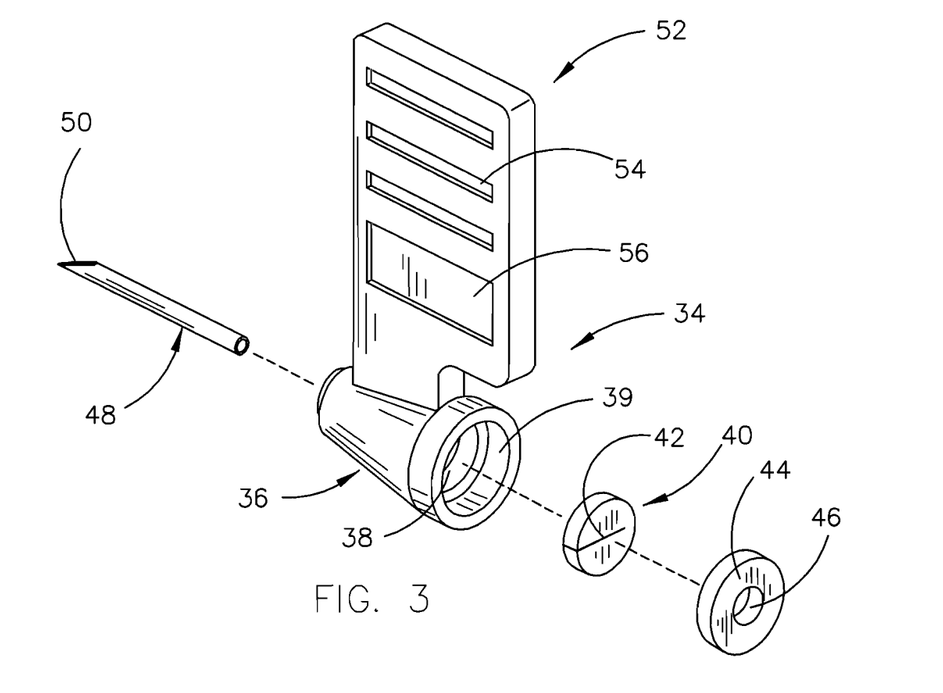
FIG. 3 is an exploded perspective view of the needle portion of the invention.
Figure 4:
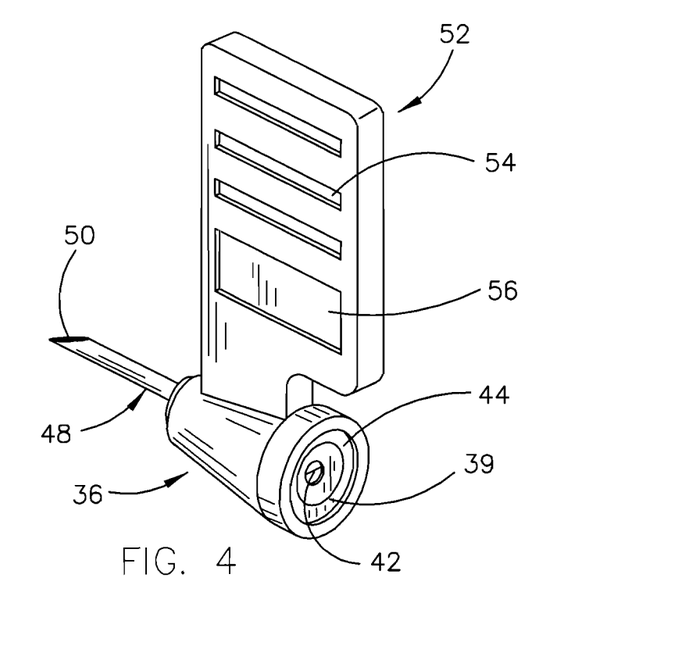
FIG. 4 is a perspective view of the needle portion of the invention.

When the insertion of the cannula 24 into the patient is to begin, the needle portion 34 will be slidably moved outwardly from its docked position of FIG. 1 to the extended position of FIG. 5 wherein the needle point 50 is positioned forwardly or outwardly of the outer or forward end 32 of shaft 30 of cannula 24 as seen in FIG. 5. The needle portion 34 is easily moved from its docked position of FIG. 1 to the extended position of FIG. 5 by the injector 62 grasping the wing 52.

Figure 8:
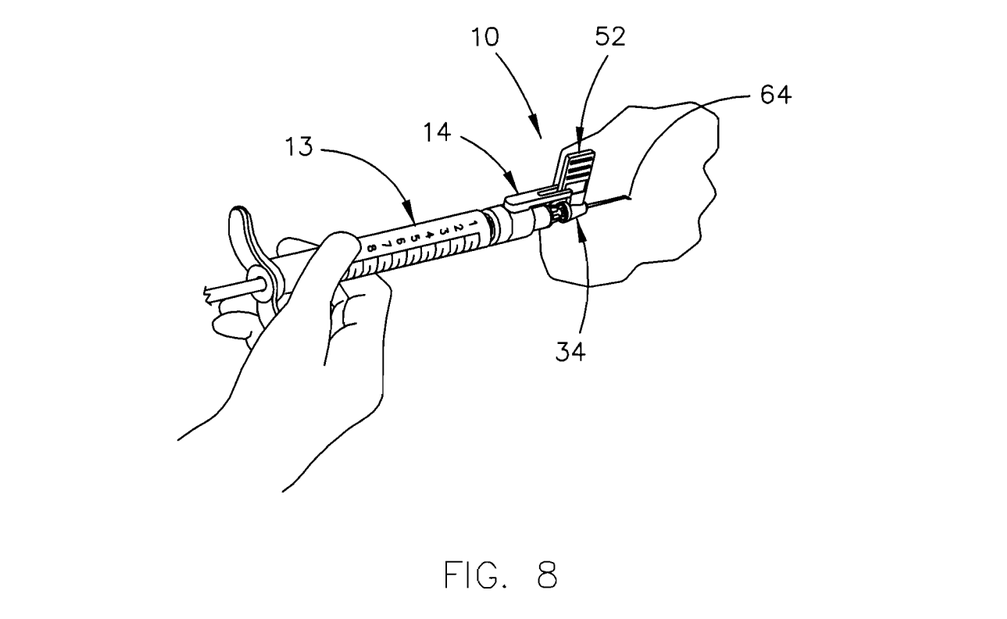
Figure 9:
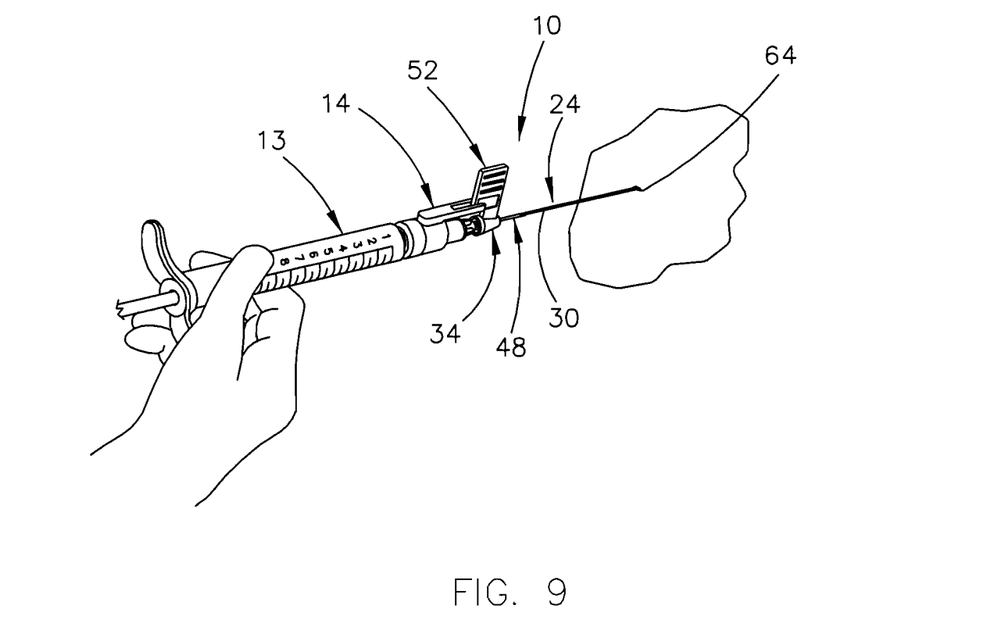

The injector 62 then causes the point 50 of needle 48 to pierce into the skin of the patient to create an opening or hole 64 in the patient. While the needle 48 is still in the hole 64, the cannula 24 is moved towards the patient so that the forward end 32 of shaft 30 of cannula 24 passes into the hole 64 under the guidance of the needle 48 to the desired location within the patient. The syringe 13 is then used to inject the medicine or cosmetic material into the patient as seen in FIG. 8. At that time, the needle portion 34 will usually be placed in its docked position so that the needle portion 34 is "out of the way". The cannula 24 may then be withdrawn from the patient or disconnected from the syringe 13 to enable the cannula 24 to be left in the patient.

Figure 10:
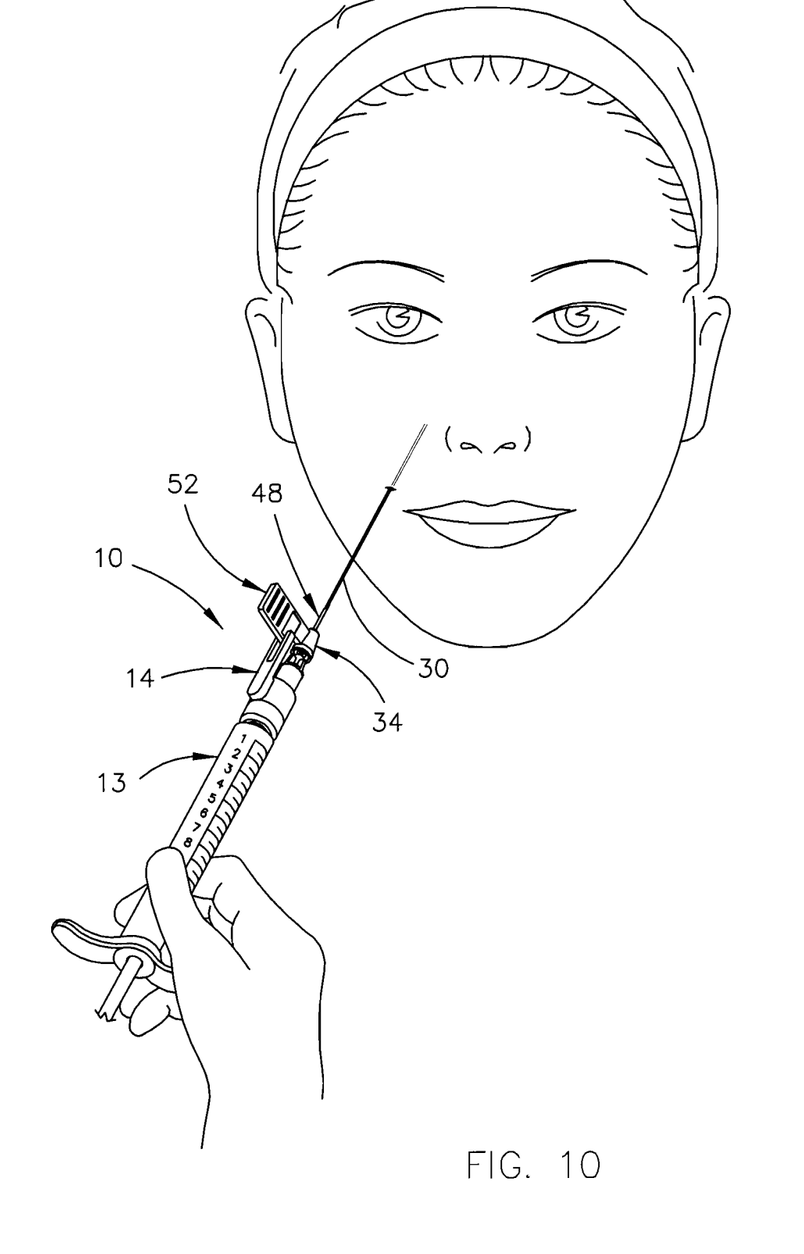
FIG. 10 is a perspective view illustrating the manner which the cannula and needle assembly of this invention is used to inject cosmetic material into the face of a patient.
Figure 11:
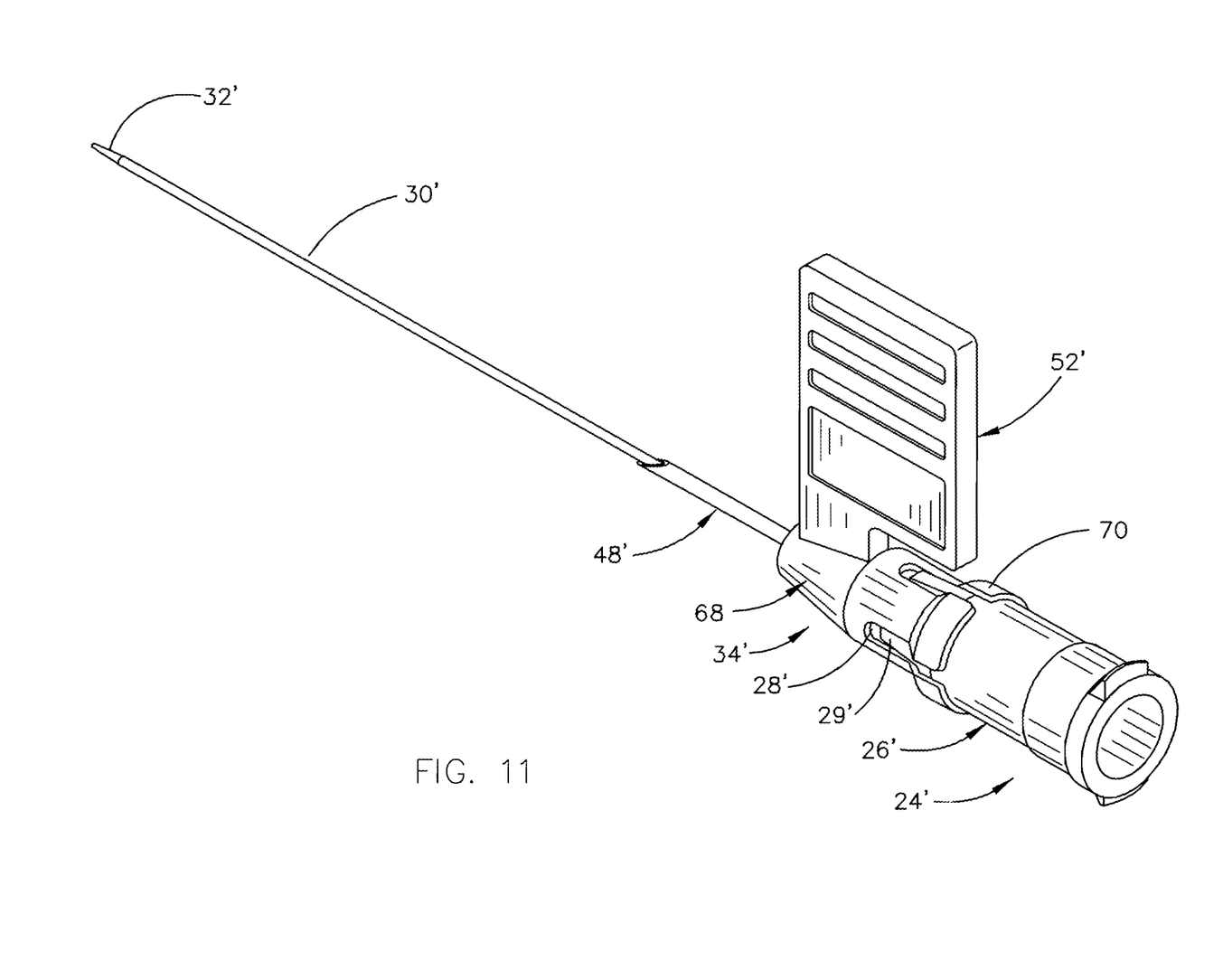
FIG. 11 is a perspective view illustrating a second embodiment of the invention.

FIG. 10 illustrates the cannula and needle assembly 10 being used to inject cosmetic material into the face of a patient.

FIG. 11 illustrates a second embodiment of the invention and which is referred to by the reference numeral 10'. The structure in FIG. 11 which is identical to the structure of the cannula and needle assembly 10 of FIGS. 1-4 is indicated with "'". The cannula and needle assembly 10' is very similar to the cannula and needle assembly 10. The cannula and needle assembly 10' illustrated in FIG. 11 does not include the needle dock 14 of cannula and needle assembly 10. Another difference between assemblies 10' and 10 is that the needle hub 68 of needle portion 34' has an enlarged rearward end 70 and has a plurality of radially spaced-apart slots 72 formed therein which receive the ribs 29' of mount 26' so that needle hub 68 is yieldably maintained in the docked position seen in FIG. 11. The cannula and needle assembly 10' is used in the way as the cannula and needle assembly 10 is used.

In summary, the needle portion 34 of the invention assists in the insertion of the cannula 24, which is dull or blunt, through the skin 60. The assembly allows an injector person to pierce the skin 60 with the needle 48 and follow with the cannula 24 without removing the needle 48 from the skin or changing hand holder on the cannula 24 and needle portion 34. Since the needle portion 34 attaches to the cannula 24, it stays sterile. The assembly 10 eliminates the step of removing the needle 48 and either recapping it or discarding it. The assembly 10 also eliminates the step that requires the injector to find the needle hole and reenter it with the cannula 24. Another advantage of the cannula and needle assembly 10 is that the assembly can be reused in different areas of the face or body, if sterility is maintained, which eliminates the need for using a new cannula and needle thereby decreasing expenses.

Although two ways are illustrated to maintain the needle hub and needle in the docked position, they could be yieldably held in the docked position by other means such as magnets, etc.

Thus it can be seen that the invention accomplishes at least all of its stated objectives.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

We claim:

1. A cannula and needle assembly, comprising:
a cannula having a rearward end and a forward end;
said cannula including a mount having rearward and forward ends with a passageway, having rearward and forward ends, extending therebetween;
said rearward end of said mount being configured to be removably connected to a syringe;
said forward end of said mount being tapered and having a plurality of radially spaced-apart ribs protruding outwardly therefrom;
said cannula including an elongated hollow shaft having a rearward end and a forward end;
said rearward of said hollow shaft being secured to said forward end of said mount whereby said rearward end of said hollow shaft is in communication with said forward end of said passageway in said mount;
a needle hub having a rearward end and a forward end;
said needle hub having a passageway formed therein which extends between said rearward and forward ends of said needle hub;
an elongated hollow needle having a rearward end and a forward end;
said rearward end of said needle being secured to said forward end of said needle hub whereby said needle is in communication with said forward end of said passageway extending through said needle hub;
said forward end of said needle being sharpened;
a wing having upper and lower ends;
said lower end of said wing being secured to said needle hub;
said rearward end of said needle hub having a plurality of radially spaced-apart slots formed therein;
said needle hub being slidably mounted on said hollow shaft of said cannula whereby said hollow shaft slidably extends through said rearward end of said needle hub, through said passageway in said needle hub and through said needle;
said needle hub and said needle being slidably movable with respect to said hollow shaft and said mount between a first docked position and a second extended position;
said slots in said rearward end of said needle hub receiving said ribs of said mount therein to yieldably maintain said needle hub and said needle in said first docked position;
said forward end of said needle being positioned rearwardly of said forward end of said hollow shaft when said needle hub and said needle are in said first docked position; and
said forward end of said needle being positioned forwardly of said forward end of said cannula when said needle hub and said needle are in said extended position.

2. The cannula and needle assembly of claim 1 wherein a seal is positioned in said needle hub and which has said hollow shaft extending therethrough with said seal frictionally engaging said hollow shaft to yieldably prevent said needle hub from slidably moving with respect to said hollow shaft.

3. The cannula and needle assembly of claim 2 wherein a seal retainer is positioned in said needle hub to maintain said seal in said needle hub.

4. The cannula and needle assembly of claim 1 wherein said wing has gripping members provided thereon.

5. The cannula and needle assembly of claim 1 wherein said rearward end of said needle hub has an enlarged portion which also has radially spaced-apart slots formed therein.

6. A cannula and needle assembly, comprising:
a cannula having a rearward end and a forward end;
said cannula including a mount having rearward and forward ends with a passageway, having rearward and forward ends, extending therebetween;
an adapter having rearward and forward ends;
said forward end of said adapter configured to be secured to said rearward end of said mount;
said rearward end of said adapter being configured to be removably connected to a syringe;
an elongated hollow shaft having a rearward end and a forward end;
said rearward of said hollow shaft being secured to said forward end of said mount whereby said rearward end of said hollow shaft is in communication with said forward end of said passageway in said mount;
a needle hub having a rearward end and a forward end;
said needle hub having a passageway formed therein which extends between said rearward and forward ends of said needle hub;
an elongated hollow needle having a rearward end and a forward end;
said rearward end of said needle being secured to said forward end of said needle hub whereby said needle is in communication with said forward end of said passageway extending through said needle hub;
said forward end of said needle being sharpened;
a wing having upper and lower ends;
said lower end of said wing being secured to said needle hub;
said needle hub being slidably mounted on said hollow shaft whereby said hollow shaft slidably extends through said rearwardly end of said needle hub, through said passageway in said needle hub and through said needle;
said needle hub and said needle being slidably movable with respect to said hollow shaft and said mount between a first docked position and a second extended position;
said forward end of said needle being positioned rearwardly of said forward end of said shaft when said needle hub and said needle are in said first docked position;
said forward end of said needle being positioned forwardly of said forward end of said cannula when said needle hub and said needle are in said extended position; and
said rearward end of said needle hub frictionally engaging said forward end of said mount to yieldably maintain said needle hub and said needle in said first docked position during times of use and non-use of the cannula and needle assembly.

7. The cannula and needle assembly of claim 6 wherein a friction seal is positioned in said needle hub and which has said shaft extending therethrough with said friction seal frictionally engaging said hollow shaft to yieldably prevent said needle hub from slidably moving with respect to said hollow shaft.

8. The cannula and needle assembly of claim 7 wherein a seal retainer is positioned in said needle hub to maintain said seal in said needle hub.

9. The cannula and needle assembly of claim 6 wherein said wing has gripping members provided thereon.

10. A cannula and needle assembly, comprising:
a cannula having a rearward end and a forward end;
said cannula including a mount having rearward and forward ends with a passageway, having rearward and forward ends, extending therebetween;
an adapter having rearward and forward ends;
said forward end of said adapter configured to be secured to said rearward end of said mount;
said rearward end of said adapter being configured to be removably connected to a syringe;
said adapter having a pair of elongated and spaced-apart detent members, having rearward and forward ends, which extend forwardly from said adapter;
an elongated hollow shaft having a rearward end and a forward end;
said rearward of said hollow shaft being secured to said forward end of said mount whereby said rearward end of said hollow shaft is in communication with said forward end of said passageway in said mount;
a needle hub having a rearward end and a forward end;
said needle hub having a passageway formed therein which extends between said rearward and forward ends of said needle hub;
an elongated hollow needle having a rearward end and a forward end;
said rearward end of said needle being secured to said forward end of said needle hub whereby said needle is in communication with said forward end of said passageway extending through said needle hub;
said forward end of said needle being sharpened;
a wing having upper and lower ends;
said lower end of said wing being secured to said needle hub;
said needle hub being slidably mounted on said hollow shaft whereby said hollow shaft slidably extends through said rearwardly end of said needle hub, through said passageway in said needle hub and through said needle;
said needle hub and said needle being slidably movable with respect to said hollow shaft and said mount between a first docked position and a second extended position;
said wing being received between said spaced-apart detent members when said needle hub and said needle are in said first docked position;
said wing being yieldably held between said detent members when said needle hub and said needle are in said first docked position;
said forward end of said needle being positioned rearwardly of said forward end of said shaft when said needle hub and said needle are in said first docked position;
said forward end of said needle being positioned forwardly of said forward end of said cannula when said needle hub and said needle are in said extended position; and
a friction seal positioned in said needle hub and which has said hollow shaft extending therethrough with said friction seal frictionally engaging said hollow shaft to yieldably prevent said needle hub from slidably moving with respect to said hollow shaft.

11. The cannula and needle assembly of claim 10 wherein a seal retainer is positioned in said needle hub to maintain said friction seal in said needle hub.

12. A cannula and needle assembly, comprising:
a cannula having a rearward end and a forward end;
said cannula including a mount having rearward and forward ends with a passageway, having rearward and forward ends, extending therebetween;
an adapter having rearward and forward ends;
said forward end of said adapter configured to be secured to said rearward end of said mount;
said rearward end of said adapter being configured to be removably connected to a syringe;
said adapter having a pair of elongated and spaced-apart detent members, having rearward and forward ends, which extend forwardly from said adapter;
an elongated hollow shaft having a rearward end and a forward end;
said rearward of said hollow shaft being secured to said forward end of said mount whereby said rearward end of said hollow shaft is in communication with said forward end of said passageway in said mount;
a needle hub having a rearward end and a forward end;
said needle hub having a passageway formed therein which extends between said rearward and forward ends of said needle hub;
an elongated hollow needle having a rearward end and a forward end;
said rearward end of said needle being secured to said forward end of said needle hub whereby said needle is in communication with said forward end of said passageway extending through said needle hub;
said forward end of said needle being sharpened;
a wing having upper and lower ends;
said lower end of said wing being secured to said needle hub;
said needle hub being slidably mounted on said hollow shaft whereby said hollow shaft slidably extends through said rearwardly end of said needle hub, through said passageway in said needle hub and through said needle;
said needle hub and said needle being slidably movable with respect to said hollow shaft and said mount between a first docked position and a second extended position;
said wing being received between said spaced-apart detent members when said needle hub and said needle are in said first docked position;
said wing being yieldably held between said detent members when said needle hub and said needle are in said first docked position;
said forward end of said needle being positioned rearwardly of said forward end of said shaft when said needle hub and said needle are in said first docked position;

said forward end of said needle being positioned forwardly of said forward end of said cannula when said needle hub and said needle are in said extended position; and said wing having gripping members provided thereon.

13. A cannula and needle assembly, comprising:

a cannula having a rearward end and a forward end;

said cannula including a mount having rearward and forward ends with a passageway, having rearward and forward ends, extending therebetween;

an adapter having rearward and forward ends;

said forward end of said adapter configured to be secured to said rearward end of said mount;

said rearward end of said adapter being configured to be removably connected to a syringe;

said adapter having a pair of elongated and spaced-apart detent members, having rearward and forward ends, which extend forwardly from said adapter;

an elongated hollow shaft having a rearward end and a forward end;

said rearward of said hollow shaft being secured to said forward end of said mount whereby said rearward end of said hollow shaft is in communication with said forward end of said passageway in said mount;

a needle hub having a rearward end and a forward end;

said needle hub having a passageway formed therein which extends between said rearward and forward ends of said needle hub;

an elongated hollow needle having a rearward end and a forward end;

said rearward end of said needle being secured to said forward end of said needle hub whereby said needle is in communication with said forward end of said passageway extending through said needle hub;

said forward end of said needle being sharpened;

a wing having upper and lower ends;

said lower end of said wing being secured to said needle hub;

said needle hub being slidably mounted on said hollow shaft whereby said hollow shaft slidably extends through said rearwardly end of said needle hub, through said passageway in said needle hub and through said needle;

said needle hub and said needle being slidably movable with respect to said hollow shaft and said mount between a first docked position and a second extended position;

said wing being received between said spaced-apart detent members when said needle hub and said needle are in said first docked position;

said wing being yieldably held between said detent members when said needle hub and said needle are in said first docked position;

said forward end of said needle being positioned rearwardly of said forward end of said shaft when said needle hub and said needle are in said first docked position;

said forward end of said needle being positioned forwardly of said forward end of said cannula when said needle hub and said needle are in said extended position; and said wing having recessed portions formed therein which receive the forward ends of said detent members when said needle hub and said needle are in said docked position.

* * * * *